US007664625B2

(12) United States Patent
Pang (10) Patent No.: US 7,664,625 B2
(45) Date of Patent: Feb. 16, 2010

(54) MOLECULAR MODELING FOR METALLOPROTEINS

(75) Inventor: Yuan-Ping Pang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 101 days.

(21) Appl. No.: 10/723,594

(22) Filed: Nov. 26, 2003

(65) Prior Publication Data

US 2004/0148149 A1 Jul. 29, 2004

Related U.S. Application Data

(62) Division of application No. 09/595,650, filed on Jun. 16, 2000, now abandoned.

(60) Provisional application No. 60/139,845, filed on Jun. 18, 1999.

(51) Int. Cl.
*G06G 7/58* (2006.01)
*G06N 7/06* (2006.01)
*G06F 19/00* (2006.01)
*G06G 7/48* (2006.01)

(52) U.S. Cl. ............................. 703/12; 702/22; 702/27; 703/11

(58) Field of Classification Search ........................ None
See application file for complete search history.

(56) References Cited

U.S. PATENT DOCUMENTS 5,553,004 A 9/1996 Gronbech-Jensen et al.

OTHER PUBLICATIONS

Chrysina et al. Crystal structures of apo- and holo-bovine a-Lactalbumin at 2.2A resolution reveal an effect of calcium on inter-lobe interactions. The Journal of Biological Chemistry. vol. 275, No. 47, 2000, pp. 37021-37029.*
Haeffner et al. Force field parameterization of copper(I)—olefin systems from density functional calculations. Journal of Molecular Structure (Theochem) vol. 297, 1997, pp. 39-50.*
Huheey et al. Inorganic Chemistry, Fourth Edition. Harper Collins College Publishers. 1993. pp. 290-292, 397-399, 401-403, and 408-413.*
Marchi et al. Solvation and ionisation of alkali metals in liquid ammonia: a path integral Monte Carlo study. Journal of Physics: Condensed Matter. vol. 2, 1990, pp. 5833-5848.*
Crawford. CH186 Lecture Presentation: Transition Metal/Coordination Chemistry. Slide 39 out of 60. Accessed [online] on Jan. 5, 2007 at < http://chemistry.semo.edu/crawford/ch186/lectures/ch20/index. html > last modified on Feb. 25, 1999.*
Maggiora. Electronic structure of porphyrins. All valence electron self-consistent field molecular orbital calculations of free base, magnesium, and aquomagnesium pophines. Journal of the American Chemcial Society, 1973, vol. 95, pp. 6555-6559.*
Zumdahl SS. Chemistry. Lexington, MA: D.C. Heath and Company, 1986, pp. 42-44 and 279-280.*
Andriotis et al. Tight-binding molecular dynamics study of transition metal carbide clusters. Chemical Physical Letters, vol. 301, Mar. 5, 1999, pp. 503-508.*

Stote et al. Zinc binding in proteins and solution: A simple but accurate nonbonded representation. Proteins: Structure, Function, and Genetics, 1995, vol. 23, pp. 12-31.*
Clemmer et al. Physical and chemical evidence for metallofullerenes with metal atoms as part of the cage. Nature. vol. 372, 1994, pp. 248-250.*
Barnett et al. J. Cryst. Mol. Struct. 1972, vol. 2, p. 271-279.*
Schlatholter et al. Collisions of Oq+ with neutral C60: charge transfer and fragmentation. J. Phys B. At. Mol. Opt. Phys. vol. 31, 1998, pp. 1321-1331.*
Niobium element facts. Obtained online on May 31, 2009 from chemicool.com/elements/niobium.html.*
Alberts et al., *Protein Science*, 1998, 7:1700-1716.
Allinger et al., *J. Mol. Struct. (Theochem)*, 1994, 69-83.
Mercandelli P., et al., *J. Am. Chem. Soc.* 1996, 118:11548-11554.
Stote et al., *Proteins*, 1995, 23:12-31.
Cornell et al. "A Second Generation Force Field for the Simulation of Proteins, Nucleic Acids, and Organic Molecules," *J. Am. Chem. Soc.*, 117: 5179-5197 (1995).
"Lennard Jones Potential," [http://en.wikipedia.org/wiki/Lennard_jones_potential], Printed on Jul. 10, 2008.
Aqvist et al., *J. Am. Chem. Soc.*, 1990, 112(8):2860-2868.
Atassi et al., *Critical Reviews in Immunology*, 1999, 19(3):219-260.
Boehm et al., *Biochem. Biophys. Res. Commun.*, 1998, 252:190-194.
Braga et al., *Chem. Commun.*, 1996, N5:571-578.
Charifson et al., *J. Computational Chem.*, 1991, 12(7):899-908.
Cieplak et al., *J. Comp. Chem.*, 1995, 16(11):1357-1377.
Cornell et al., *J. Am. Chem. Soc.*, 1995, 117(19):5179-5197.
El Yazal et al., *J. Phys. Chem. B*, 1999, 103:8773-8779.
El Yazal et al., *J. Phys. Chem. B*, 2000, 104:6662-6667.
Guilbaud et al., *J. Phys. Chem.*, 1993, 97:5685-5692.
Hanahan et al., *Cell* 1996, 86(3):353-364.
Hoops et al., *J. Am. Chem. Soc.*, 1991, 113(22):8262-8270.
Klimpel et al., *Mol. Microbiol.*, 1994, 13(6):1093-1100.
Lu et al., *Proteins*, 1998, 33:119-134.
Mackay et al., *Trends Biochem. Sci.*, 1998, 23:1-4.
Pang et al., *J. Am. Chem. Soc.*, 1999, 121(8):1717-1725.
Pang, *J. Mol. Model.*, 1999, 5:196-202.
Roe et al., *J. Mol. Model.*, 1999, 5:134-140.
Ryde, *Proteins*, 1995, 21:40-56.
Santos et al., *Clin. Exp. Metastasis*, 1997, 15:499-508.
Schneider et al., Pure & Appl. Chem., 1993, 65(11):2329-2334.
Shalinsky et al., *Annals of Oncology*, 1998, 9(2):73, Abstract No. 278.
Shalinsky et al., *Clin. Cancer Res.*, 1999, 5(7):1905-1917.
Sivaraja et al., *J. Am. Chem. Soc.*, 1992, 114(9600-9603.
Vanhooke et al., *Biochem.*, 1996, 35(19):6020-6025.
Vedani et al., *J. Am. Chem. Soc.*, 1990, 112(12):4759-4767.
Vu et al., *Cell*, 1998, 93(3):411-422.
Wasserman et al., *Proteins*, 1996, 24(2):227-237.
Zahn et al., *J. Am. Chem. Soc.*, 1999, 121(32):7279-7282.

* cited by examiner

*Primary Examiner*—Marjorie Moran
*Assistant Examiner*—Russell S Negin
(74) *Attorney, Agent, or Firm*—Fish & Richardson P.C.

(57) ABSTRACT

A method for designing a metal ion for use in a molecular dynamics simulation can include the steps of building a metal ion molecule having a center atom and a dummy atom, assigning a van der Waals radius to the center atom, and assigning a charge to the dummy atom. A metal ion molecule may have the center atom covalently linked to one or more dummy atoms resulting in the metal ion molecule having a polyhedron geometry. New force field parameters may be used in methods for designing metal ions for use in molecular dynamics simulations.

17 Claims, 7 Drawing Sheets

MOLECULAR MODELING FOR METALLOPROTEINS

CROSS-REFERENCE TO RELATED APPLICATION

This application is a divisional of U.S. patent application Ser. No. 09/595,650, filed Jun. 16, 2000, now abandoned entitled, "Molecular Modeling for Metalloproteins", which claims the benefit of priority under 35 U.S.C. §119 of U.S. Provisional Patent Application Ser. No. 60/139,845, filed on Jun. 18, 1999, entitled, "Molecular Modeling for Metalloproteins".

FIELD OF THE INVENTION

The invention relates to molecular dynamics simulations for metals. In particular, the invention relates to molecular dynamics simulations involving metalloproteins.

BACKGROUND OF THE INVENTION

An increasing number of researchers use molecular dynamics (MD) simulations for research purposes such as identifying potential new drugs, identifying potential sites to mutate known proteins, and simulating protein-ligand interactions.

Two accepted methods have been reported for MD simulations of metalloproteins, such as the known zinc-bound proteins. The first is commonly referred to as the "bonded model." The bonded model imposes a covalent bond between a metal cation, e.g., zinc, and its ligands to maintain the polyhedral geometry of the cation and its ligands during the MD simulations. There are disadvantages for the bonded model method including the inability to evaluate the intermolecular interactions of the metal cations with their ligands and the inability to simulate the exchanges of the ligands that coordinate to the metal ion. The second method is commonly referred to as the "non-bonded model." The non-bonded model maintains a metal ion's geometry, e.g., zinc's polyhedral geometry, with electrostatic and van der Waals forces. The non-bonded model, however, is limited by the instability of such geometries during nanosecond MD simulations.

Accordingly, a dilemma facing researchers is the limitations of the conventional bonding models and methods for modeling bonding interactions of metal ions. Thus, there exists a need for improved methods for modeling metal-containing proteins.

SUMMARY OF THE INVENTION

A method for MD simulations of metalloproteins including transition metal ions such as zinc includes the step of creating a simulated polyhedral metal ion having a center atom and at least one dummy atom wherein the dummy atom may not have van der Waals interactions with other atoms. The method may use a positively charged dummy atom to represent a metal ion's vacant electronic orbital that accommodates the lone-pair electrons of the metal ion's coordination ligand. The method may use a center atom to represent the van der Waals radius of a metal ion. The method may be effective for imposing the orientational requirement for the metal ion's coordination ligand, in maintaining the polyhedron geometry of a metal ion's coordination complex in proteins during MD simulations and in simulating charge-transfer effects of transition or main group metal ions. The method alleviates the shortcomings of the conventional methods, and enables a researcher to evaluate intermolecular interactions of the metal cation with its ligands in proteins and other synthetic hosts, simulate the metal ion's polyhedral complex, and simulate the exchange of ambidentate ligands of the metal ion coordination complex in proteins.

In one aspect, the invention features a method for designing a metal ion for use in a MD simulation including the steps of: a) building a metal ion molecule having a center atom and a dummy atom; b) assigning a van der Waals radius to the center atom; and c) assigning an atomic charge to the dummy atom, wherein the center atom and the dummy atom are covalently bonded, and wherein the metal ion has a polyhedron geometry. In one embodiment, dummy atoms are located at the apices of a polyhedron.

In one embodiment, one or more of the dummy atoms simulate a vacant electronic orbital of the metal ion. The vacant electronic orbital can accommodate the lone-pair electrons of a coordination ligand of the metal ion thereby imposing an orientational requirement for a coordination ligand of the metal ion. The metal ion can maintain its polyhedral geometry of the metal ion coordination complex in a nanosecond or longer length protein MD simulation, in a computer-aided protein-ligand docking simulation, in an organic molecule simulation, in an inorganic molecule simulation, in simulating charge transfer effects of a transition metal ions and/or in an energy refinement.

Useful metal ions include zinc, cadmium, mercury, copper, nickel, cobalt, iron, manganese, calcium, magnesium, and any other main group and/or transition metal ion.

In another aspect, the invention features a method for performing nanosecond or longer MD simulations including the steps of: a) assigning the force field parameters of Table 1 to a metal ion; and b) performing a nanosecond or longer MD simulation. Such a method can be combined with any of the embodiments of the previously described method.

In some embodiments, the dummy atoms used in any of the methods described herein have a charge of less than about +3, less than about +2, less than about +1, ranging from about +0.1 to about +3, ranging from about +0.2 to about +0.8, +0.3333, +0.4, or +0.5. Additionally, the dummy atoms may have no van der Waals interaction with other atoms, i.e., r*=0 & e=0. A central atom may have a van der Waals radius and an atomic charge of zero. The van der Waals radius of the center atom may approximate the van der Waals radius of the metal ion it is simulating.

The force field parameters and methods disclosed herein are particularly useful for developing pharmaceutically effective drugs or compounds and for designing transcription factors used in gene therapy.

The methods and force field parameters disclosed herein can produce excellent agreement between X-ray crystallographic analyses and 2.0 ns MD simulations of zinc-bound proteins including farnesyltransferase, endostatin, carbonic anhydrase, carboxypeptidase A, rubredoxin, and phosphotriesterase. The methods and force field parameters disclosed herein facilitate designing improved endostatin mimetics, zinc finger mutants, phosphotriesterase mutants, and inhibitors of anthrax and botulinum toxins.

A simulated metal ion molecule for use in a molecular dynamics simulation includes a center atom having a van der Waals radius greater than zero covalently linked to one or more dummy atoms having a van der Waals radius of about zero, wherein the overall charge of the metal ion molecule is evenly distributed among the dummy atoms and wherein the center atom has a charge of zero. The dummy atoms can be assigned a mass of about 0.1 or greater that about 0.1. The simulated metal ion molecule can have the dummy atoms located at the apices of a polyhedron and the center atom may be at the center of the polyhedron. Useful polyhedrons include trigonal, tetrahedron, pentahedron, hexagonal, septagonal, and octahedral. Useful metals include main group and transition metals such as zinc, cadmium, mercury, copper, nickel, cobalt, iron, manganese, calcium, and magnesium.

In some embodiments, the simulated metal ion molecule may have a calculated energy of solvation about equal to an experimentally determined energy of solvation for the actual metal ion. At times, the calculated energy of solvation is within about 10% of the experimentally determined energy of solvation for the metal ion.

The charge of the simulated metal ion molecule can vary. It may be a charge of about +0.3333, +0.5, or range from about +0.1 to about +3.

An advantage of the disclosed force field parameters, metal ion molecules, and methods is that they provide a better understanding of the nature of metal ligand coordination., and enable proper evaluation of thermodynamic quantities such as free energy of binding contributed by the conformational fluctuations of the metal-binding site. Furthermore, the disclosed force field parameters and methods offer a means for refining the X-ray structures of metal-containing proteins in which the carboxylate does not serve as an ambidentate ligand and when an electron density map cannot determine which oxygen atom of the carboxylate should coordinate to the metal such as zinc.

Unless otherwise defined, all technical and scientific terms used herein have the same meaning as commonly understood by one of ordinary skill in the art to which this invention belongs. Amino acids have been designated herein by standard three letter and one-letter abbreviations. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following drawings, detailed description, and claims.

DETAILED DESCRIPTION

The inventor has observed that the tetrahedral geometry of the zinc coordination complex identified in the x-ray structure of farnesyltransferase changed to an octahedron in MD simulations of zinc-containing farnesyltransferase using the computer program AMBER 5.0 (TM) despite using alternative parameters developed within the paradigm of the known non-bonded model for MD simulations. While not being bound to a particular mode of action, the instability problem appeared to be due to the fact that the force field parameters of the zinc ion in the non-bonded model were developed using a zinc ion that was liganded to six water molecules. Simulations of a tetrahedral zinc coordination complex with the same force field parameters resulted in a conversion to an octahedral complex if the tetrahedral zinc coordination complex was exposed to water for about 1 pico second during the MD simulation. Conceptually, it was thought that the instability problem was due to the simplification that zinc's coordination geometry was solely determined by the repulsion among the zinc ligands. As a consequence, the inventor has discovered a method for evaluating metal-ligand interactions (collectively referred to as a coordination complex) in metalloproteins that can maintain the desired geometries for the metal ion coordination complexes contained within a metalloprotein.

A useful method for modeling metal containing proteins includes modifying the metal ion geometries and metal ion parameters for the metal ion in a MD simulation computer program. The method can be used for main group and transition metals including zinc, cadmium, mercury, copper, nickel, cobalt, iron, manganese, calcium, and magnesium. Conventional metal ion coordination complex geometries are known and any MD simulation program can be used. A particularly useful program is the AMBER 5.0 (TM) program. AMBER refers to Assisted Model Building and Energy Refinement which uses the potentials developed by Peter Kollman. AMBER is known to those of ordinary skill in the art. The orientation effect of the electronic nature of transition metals can be effectively modeled allowing the investigator to mimic charge transfer effects of metals.

For example, zinc ions found in known crystal structures of zinc containing proteins can be classified into five- and six-ligand coordination patterns or complexes. Alberts et. al., "Analysis of Zinc Binding Sites in Protein Crystal Structure," Protein *Science*, vol. 7, pp. 1700-1716 (1998). Experimental observations of five- and six-ligand complexes using x-ray crystallography and other spectroscopic methods show that one or two pairs of the ambidentate ligands exchange over time and can be averaged as bidentate ligands. Ab initio calculations of proton dissociation energies of common zinc ligands show that imidazole rings exist as an imidazolate when coordinated to $Zn^{2+}$ in proteins. Thiols and peptide nitrogen atoms are also known to exist in the deprotonated form when coordinated to $Zn^{2+}$ in proteins.

Detailed review of known zinc containing proteins indicated that the zinc ion was in a tetrahedral configuration and thus the zinc divalent cation should be coordinated to four ligands for MD simulations. The four-ligand coordination complex can be favorable for zinc because zinc's electronic structure accommodates, in terms of energetics, four pairs of electrons in its vacant $4s4p_x4p_y4p_z$ orbitals. In other words, zinc's coordination geometry can be determined mainly by its electronic structure and not by the repulsion among the zinc ligands. In this manner, the zinc ion should be maintained in a tetrahedral configuration.

Persons of ordinary skill in the art know how to create and modify molecules and ligands in MD simulation computer programs. Using the information provided herein, a tetrahedral zinc model can be created and used in MD simulations when modeling zinc containing proteins. The tetrahedral zinc model can include two important features. First, the $Zn^{2+}$ ion can be replaced with a five-atom molecule referred to herein as a tetrahedral zinc molecule. The tetrahedral zinc molecule facilitates maintaining the tetrahedral zinc coordination complex in a protein. Second, one or more of the metal coordination ligands that coordinate the zinc ion can be deprotonated. In this instance, the metal coordination ligands can be referred to as zinc ligands. Useful metal coordination ligands, such as zinc ligands, include protein side chain and backbone atoms capable of forming a noncovalent bonds or interactions with the metal ion. Metal coordination ligands may also include water molecules. Useful metal coordination ligands include tryptophan, serine, threonine, tyrosine, asparagine, glutamine, aspartic acid, glutamic acid, histidine, and the carbonyl oxygens. The metal coordination ligands should be capable of forming a thiolate, imidazolate, carboxylate, amidate, and/or contain a hydroxide group. Preferably, all of the metal ligands are deprotonated in the MD simulation.

A tetrahedral zinc molecule having a tetrahedral configuration has five atoms. One atom is located at the center of the zinc molecule. This center atom is assigned the total size of the molecule, i.e., the center atom should encompass the Lennard-Jones parameters for the tetrahedral zinc molecule. The center atom is not assigned a charge. The remaining four atoms are covalently bound to the center atom and are referred to as dummy atoms. A dummy atom is defined as an atom that is assigned a van der Waals size of zero. That is, a dummy atom is basically a point charge. Dummy atoms thus do not sterically interact with other atoms, since their Lennard-Jones steric interaction parameters ($r^*$ and $\epsilon$) in a MD simulation program such as AMBER 5.0 (TM) are set to zero. The dummy atoms do, however, carry a charge. In particular, it is advantageous to assign a fraction of the total charge of the ion to each dummy atom. The total charge of the molecule may be evenly distributed between all of the dummy atoms. For example, in a tetrahedral zinc molecule having a total charge of +2, each dummy can be assigned a +0.5 charge. Furthermore, dummy atoms are assigned a mass. Typically, the mass is about 0.1 but other masses may also be useful.

Figure 1:
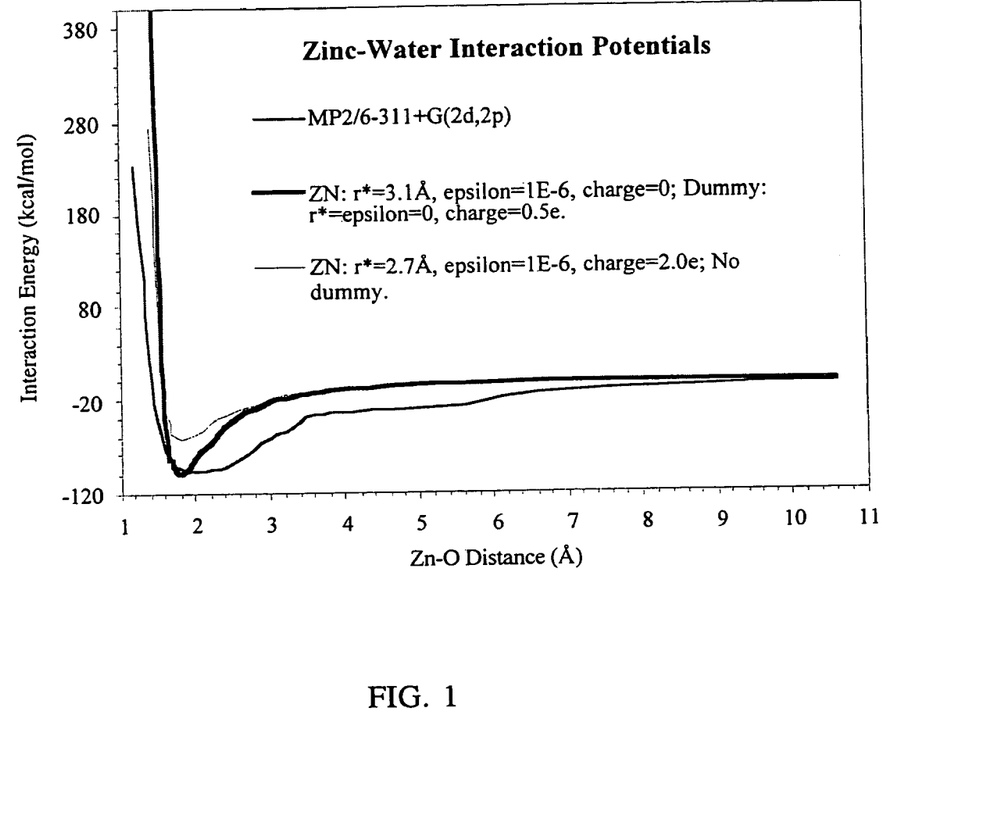
FIG. 1 depicts the zinc-water interaction potentials calculated by quantum mechanics (medium) and molecular mechanics with the tetrahedral zinc molecule (bold) and with the conventional zinc ion (thin).

Table 1 shows the bonded parameters of the tetrahedral zinc ion (ZN=$ZN^{2+}$ and DZ=dummy atom having a mass of 0.1, for non-bonded parameters see FIG. 1) and the RESP charges of histidinate and hydroxide (for definitions of the atom names see Cornell et al., "A Second Generation Force Field for the Simulation of Proteins and Nucleic Acids," *J. Am. Chem. Soc.* 117, 5179-5197 (1995).).

TABLE 1

The Force Field Parameters of the Tetrahedral Zinc Ion

| Bond | K [kcal/(mol Å$^2$)] | $R_{eq}$ (Å) |
|---|---|---|
| DZ-ZN | 540.0 | 0.90 |
| DZ-DZ | 540.0 | 1.47 |

| Angle | K [kcal/(mol rad$^2$)] | $T_{eq}$ (deg.) |
|---|---|---|
| DZ-ZN-DZ | 55.0 | 109.50 |
| DZ-DZ-DZ | 55.0 | 60.0 |
| DZ-DZ-ZN | 55.0 | 35.25 |

| Torsion | IDIVF | $V_n/2$ | γ (deg.) | n |
|---|---|---|---|---|
| ZN-DZ- | 1 | 0.0 | 35.3 | 2. |
| DZ-ZN- | 1 | 0.0 | 120.0 | 2. |
| DZ-DZ- | 1 | 0.0 | 70.5 | 2. |

The RESP Charges of Histidinate

| Atom | Charge |
|---|---|
| N | −0.5641 |
| H | 0.2469 |
| CA | 0.3171 |
| HA | 0.0096 |
| CB | −0.1347 |
| HB2 | 0.0083 |
| HB3 | 0.0381 |
| CG | 0.1504 |
| HO | 0.2049 |
| ND1 | −0.7626 |
| CE1 | 0.4994 |
| HE1 | −0.0295 |
| NE2 | −0.7656 |
| CD2 | 0.0405 |
| HD2 | 0.0525 |
| C | 0.4588 |
| O | −0.5653 |
| OH | −1.2049 | rad = radian.

To force a zinc coordination ligand to form a tetrahedral complex with zinc, dummy atoms can be placed at the four apices of a tetrahedron with the zinc ion located at the center of the tetrahedron. The dummy atoms therefore represent zinc's four vacant $4s4p_x4p_y4p_z$ orbitals. Energy minimizations of highly distorted zinc-containing protein structures can sometimes cause drastic deformations of the geometry of the tetrahedral zinc molecule. However, deformations can be avoided by introducing a covalent bond between the dummy atoms. Alternatively, a highly distorted zinc-containing protein can undergo an energy minimization structure employing harmonic restraints on the tetrahedral zinc molecule and its ligands followed by another energy minimization without the harmonic restraints.

In the tetrahedral zinc model, the zinc-bound imidazole ring or the zinc-bound water molecule can be deprotonated as an imidazolate or a hydroxide [(see, ElYazal and Pang, "Ab initio Calculations of Proton Dissociation Energies of Zinc Ligands: Hypothesis of Imidazolate as Zinc Ligand in Proteins", J. Phys. Chem. B, in press) (2000)]. Also, the carboxylate group of Asp and Glu can be protonated when the imidazolate or the hydroxide forms a hydrogen bond with such a carboxylate. Moreover, the same protonation states of the water molecule, imidazole ring, and carboxylate group can be used when the interactions between the zinc-bound water (or the zinc-bound imidazole ring) and the carboxylate group are bridged by a water molecule or the hydroxyl group of Ser or Thr. [(see ElYazal and Pang, "Zinc's Effect on Proton Transfer between Imidazole and Acetate Predicted by ab Initio Calculations", J. Phys. Chem. B, in press (2000)].

It may be helpful to adjust the van der Waals radius of the center atom of the zinc tetrahedron molecule (or other transition metal polyhedron molecule) so as to provide a molecule having an energy of solvation that is about the same as experimentally derived energies of solvation for the particular ion. For example, the molecular mechanics calculated energy of solvation for the conventional zinc ion and the tetrahedral zinc molecule were found to be much smaller than the reported experimental values presumably because of the under-evaluation of zinc's interaction energy caused by a neglect of polarization in the additive force field by Cornell et al. "A Second Generation Force Field for the Simulation of Proteins and Nucleic Acids," *J. Am. Chem. Soc.* 117. 5179-5197 (1995). To minimize the difference in zinc's solvation energy between the experimental and calculated values, the van der Waals radius of the zinc ion in the tetrahedral zinc molecule was reduced from 3.3 Å to 3.1 Å in order to strengthen the interaction of the zinc ion with its ligands. Shortening the van der Waals radius reduced the Zn—S distance by 0.2 Å in MD simulations compared to an average Zn—S distance of 2.3±0.1 Å obtained from a survey of available zinc protein crystal structures. Reducing the van der Waals radius of the tetrahedral zinc molecule caused a concomitant change in the calculated zinc solvation energy (−448 kcal/mol), which was about 8% smaller than the experimental measurement of −485 kcal/mol. The force field parameters of the tetrahedral zinc molecule thus represented a balance between the zinc ligand distances and the zinc ligand interaction energies in MD simulations.

As shown in FIG. 1, the interaction surface obtained from ab initio calculations reveals a flat region, i.e., the Zn—O distance ranges from 1.8 to 2.0 Å, where a minimal energy (maximal association energy) of −94.6 kcal/mol can be obtained (MP2/6-311+G(2d,2p)). The interaction surface derived from molecular mechanics calculations using the tetrahedral zinc molecule produced a minimal energy of −103.0 kcal/mol at the Zn—O distance of 1.8 Å (ZN: r*=3.1 Å, epsilon=1E-6, charge=0.0, DZ, r*=epsilon=0, charge=0.5). The interaction surface derived from quantum mechanics calculations with the traditional zinc ion yielded a minimum of −61.5 kcal/mol at the same Zn—O distance (ZN, r*=2.7 Å, epsilon=IE-6, charge=2.0, noDZ). The tetrahedral zinc molecule significantly alleviated the inherent problem of the under-evaluation of zinc's interaction energy.

It is to be understood that other polyhedron arrangements may be needed or preferred for other metal ions. For instance, magnesium is known to be bound in an octahedral configuration. Thus, the six dummy atoms in an octahedral $Mg^{2+}$ molecule may each be assigned an atomic charge of +0.3333 and can be placed at the individual apices of an octahedron (see Table 2). The same method can be applied to octahedral calcium coordination complexes (see Table 3). The various polyhedron arrangements for other metal ions can be derived from known crystal structures and the art in general. A person of ordinary skill in the art knows how to identify the appropriate polyhedron arrangement for metals in proteins. Known polyhedron arrangements include trigonal, tetrahedron, pentahedron, hexagonal, septagonal, and octahedral.

TABLE 2

The force field parameters of the octahedral magnesium divalent cation (Mg = $Mg^{2+}$, Da = Db = Dc = Dd = De = Df = dummy atom with mass of 0.1).

| bond | K [kcal/(mol Å$^2$)] | $R_{eq}$ (Å) |
|---|---|---|
| Mg-Da | 540.0 | 0.90 |
| Mg-Db | 540.0 | 0.90 |
| Mg-Dc | 540.0 | 0.90 |
| Mg-Dd | 540.0 | 0.90 |
| Mg-De | 540.0 | 0.90 |
| Mg-Df | 540.0 | 0.90 |

| angle | K [kcal/(mol radian$^2$)] | $T_{eq}$ (deg.) |
|---|---|---|
| Da-Mg-Db | 30.0 | 90.0 |
| Da-Mg-Dc | 30.0 | 180.0 |
| Da-Mg-Dd | 30.0 | 90.0 |
| Da-Mg-De | 30.0 | 90.0 |
| Da-Mg-Df | 30.0 | 90.0 |
| Db-Mg-Dc | 30.0 | 90.0 |
| Db-Mg-Dd | 30.0 | 180.0 |
| Db-Mg-De | 30.0 | 90.0 |
| Db-Mg-Df | 30.0 | 90.0 |
| Dc-Mg-Dd | 30.0 | 90.0 |
| Dc-Mg-De | 30.0 | 90.0 |
| Dc-Mg-Df | 30.0 | 90.0 |
| Dd-Mg-De | 30.0 | 90.0 |
| Dd-Mg-Df | 30.0 | 90.0 |
| De-Mg-Df | 30.0 | 180.0 |

| nonbonded | R* (Å) | E (kcal/mol) |
|---|---|---|
| Mg | 2.9 | 1.0E-6 |
| Da | 0.0 | 0.0 |

TABLE 3

The force field parameters of the octahedral calcium divalent cation (Ca = $Ca^{2+}$, Da = Db = Dc = Dd = De = Df = dummy atom with mass of 0.1).

| bond | K [kcal/(mol Å$^2$)] | $R_{eq}$ (Å) |
|---|---|---|
| Ca-Da | 540.0 | 0.90 |
| Ca-Db | 540.0 | 0.90 |
| Ca-Dc | 540.0 | 0.90 |
| Ca-Dd | 540.0 | 0.90 |
| Ca-De | 540.0 | 0.90 |
| Ca-Df | 540.0 | 0.90 |

| angle | K [kcal/(mol radian$^2$)] | $T_{eq}$ (deg.) |
|---|---|---|
| Da-Ca-Db | 30.0 | 90.0 |
| Da-Ca-Dc | 30.0 | 180.0 |
| Da-Ca-Dd | 30.0 | 90.0 |
| Da-Ca-De | 30.0 | 90.0 |
| Da-Ca-Df | 30.0 | 90.0 |
| Db-Ca-Dc | 30.0 | 90.0 |
| Db-Ca-Dd | 30.0 | 180.0 |
| Db-Ca-De | 30.0 | 90.0 |
| Db-Ca-Df | 30.0 | 90.0 |
| Dc-Ca-Dd | 30.0 | 90.0 |
| Dc-Ca-De | 30.0 | 90.0 |
| Dc-Ca-Df | 30.0 | 90.0 |
| Dd-Ca-De | 30.0 | 90.0 |
| Dd-Ca-Df | 30.0 | 90.0 |
| De-Ca-Df | 30.0 | 180.0 |

| nonbonded | R* (Å) | E (kcal/mol) |
|---|---|---|
| Ca | 3.6 | 1.0E-6 |
| Da | 0.0 | 0.0 |

A use for the geometry-dependent MD simulations of metalloprotein includes computational methods for identifying angiogenesis inhibitors. The parameters and methods described herein provide an approach for evaluating the free energy of binding for zinc ligands, for simulating zinc's tetrahedral complex, and for simulating the exchange of zinc's ambidentate ligands in proteins. This approach as described below may expedite the search for effect angiogenesis inhibitors to combat cancers.

Angiogenesis is the formation of new blood vessels induced by tumors as a lifeline for oxygen and nutrients and as exits for spread of cancer cells. Blocking a tumor's blood supply can starve tumors, thus saving cancer patients. The blocking effect is termed anti-angiogenesis. Matrix metalloproteases (MMPs) are a class of proteins with $Zn^{2+}$ bound in the active site that cleave the constituents of the extracellular matrix and control angiogenesis. MMPs such as MMP-s, MMP-9 and MT-MMPs have recently been identified as a class of new, promising drug targets for anti-angiogenesis. See Hanahan & Folkman, "Patterns And Emerging Mechanisms of the Angiogenic Switch During Tumorigenesis, *Cell* 86, 353-364 (1996); Vu, T. H. et al. "Mmp-9/Gelatinase B Is a Key Regulator of Growth Plate Angiogenesis and Apoptosis of Hypertrophic Chondrocytes." *Cell* 93, 411-422 (1998); Santos et. al., "Pharmacokinetic and Anti-Tumor Efficacy Studies With a Series of Synthetic Inhibitors of Matrix Metalloproteinases." *Clinical & Experimental Metastasis* 15, 499-508 (1997); Shalinsky et al., "AG3340, A Novel MMP-inhibitor, Has A Superior Therapeutic Index To Carboplatin In Nude Mice Bearing Chemoresistant Human MV522 Lung Cancer Tumors," *Annals Of Oncology* 9 (Suppl. 2), 278 (1998); Shalinsky et al., "Marked Inhibition Of Proliferation Of Human Adenocarcinoma Colon Tumores in vivo By Orally Administered AG3340. A Novel Matrix Metalloproteinase Inhibitor," *Cancer Res.* (in press). Development of new selective MMP-inhibitors is traditionally based on an iterative crystal structure approach. For example, an MMP-inhibitor can be constructed so as to conform to the binding site of an MMP having a known crystal structure. Then, the inhibitor can be iteratively modified by basing the new structure on a subsequent crystal structure of the MMP complexed with the inhibitor and further modified inhibitors. This approach, however, is expensive, time-consuming and fortuitous because of the unpredictable growth of well diffracting protein crystals. The search may be expedited by combining the crystal structure approach with a computational approach so that the binding affinity of the designed inhibitors can be estimated computationally on the basis of the first crystal structure before launching the experimental work. One way to do this is to estimate the binding affinity of the designed MMP-inhibitors by using the solvent and entropy effects of the protein complex in an MD simulation of the MMP-Inhibitor complexes where the binding of the MMP-inhibitor is mediated by the zinc ion, preferably with the zinc simulated using a tetrahedral zinc molecule.

In addition, the metal ion complexes and methods disclosed herein are useful for designing inhibitors targeted to the anthrax toxin lethal factor and the light chain region of botulism toxins. These toxins have been identified as having zinc containing proteases. See Atassi et al., "Structure, Activity, and Immunue (T and B cell) Recognition of Botulism Neurtoxins," *Critical Reviews in Immunology*, 19(3): 219-60 (1999); Klimpel et al., "Anthrax Toxin Lethal Factor Contains a Zinc Metalloproteins Censesu Sequence which is Required for Lethal Toxin Activity." *Molecular Microbioloby*, 13(6): 1093-1100 (1994).

The tetrahedral zinc method can be demonstrated using MD simulations of carbonic anhydrase (PDB code: 1ca2), carboxypeptidase A (PDB code: 5 cpa), rubredoxin (PDB code: 1 irn), and phosphotriesterase (PDB code: 1 dpm) in water at 25° C. It is to be understood that carbonic anhydrase, carboxypeptidase A, and rubredoxin and phosphotriesterase are illustrative representations of zinc-binding proteins. Accordingly, the invention will be further described in the following examples, which do not limit the scope of the invention described in the claims.

EXAMPLE 1

Molecular Modeling Using a Tetrahedral Zinc Molecule

All molecular mechanics calculations were performed using the AMBER 5.0 (TM) program with the Cornell et al. force field and additional parameters in Table 1 and FIG. 1 according to a slightly modified literature procedure. The literature procedure was reported in Pang et. al., "Computational and Experimental Studies of (2,2)-Bis(indol-1-yl-methyl)acetate Suggest the Importance of the Hydrophobic Effect in Aromatic Stacking Interactions," *J. Am. Chem. Soc.* 121, 1717-1725 (1999). The modification was the inclusion of the Particle Mesh Ewald (PME) method (see below) during the simulation and the inclusion of the parameters in Table 1.

Unless otherwise indicated, the remaining parameters for the AMBER 5.0 (TM) program were the default parameters. A distance cutoff of 8.0 Å was used for calculating the non-bonded steric interactions. PME method was used for calculating the electrostatic interactions. The non-bonded atom pair list was updated at every 20 steps in the MD simulations. All three proteins were solvated in a TIP3P water box with a periodic boundary condition (CUTX=CUTY=CUTZ=8.2). The solvated proteins were energy minimized for 500 steps before heating in order to remove close van der Waals contacts in the proteins.

In the calculations of zinc's solvation free energy, a distance cutoff of 15.0 Å was used for calculating the non-bonded steric and electrostatic interactions. The tetrahedral zinc molecule was solvated in a TIP3P water box with a periodic boundary condition (CUTX=CUTY=CUTZ=15.5). The zinc solvation energy was computed along two different perturbation paths, and included the Born correction, which accounts, in part, for the error introduced by use of a finite truncation for the electrostatic interaction. The first perturbation was to perturb the tetrahedral zinc molecule directly to null during a 1.0 ns MD simulation. The second perturbation was to perturb the tetrahedral zinc molecule to methane and then to null during a 2.0 ns MD simulation. The difference in solvation energy between the two methods was 0.8 kcal/mol, indicating that the calculated solvation energies had converged.

The RESP charges of histidinate and hydroxide were calculated by the Gaussian 94 (TM) program and the AMBER 5.0 (TM) program according to the literature procedure. Cieplak et al., "Application of the Multimolecule and Multiconformational RESP Methodology to Biopolymers: Charge Derivation for DNA, RNA, and Proteins," *J. Comp. Chem.*, 16:1357-1377 (1995). The charges of histidinate were averaged from the charges of two histidinates with different populated side-chain conformations.

Simulation of Carbonic Anhydrase All the Glu and Asp residues were deprotonated except for Glu106 and Glu117. All the Arg and Lys residues, His4, His10, His36, His107 and Cys206 were protonated. His15, His17 and His64 were assigned as HIE ($N^\delta$—H) tautomer except for His 122 as HID ($N^\delta$—H) tautomer. His94, His96, His119 and $H_2O265$ were treated as histidinate and hydroxide, respectively. Lys24, Arg27, Lys39, Asp72, Glu221, and Arg246 were each neutralized by adding a counter ion ($Na^+$ or $Cl^-$), respectively. The parameters for the PME method were defined as follows:

BOXX=72.3387, BOXY=66.2812, BOXZ=62.7392, ALPHA=BETA=GAMMA=90.0. NFFTX=64, NFFTY=64. NFFTZ=64, SPLINE_ORDER=4, ISCHARGED=0, EXACT_EWALD=0, DSUM_TOL=0.00001.

Simulation of Carboxypeptidase A All the Glu and Asp residues were deprotonated except for Asp142 and Glu270. All the Arg and Lys residues, His13, His29, His120, and His303 were protonated. His186 and His166 were assigned as HIE and HID, respectively. His69, His196, and $H_2O313$ were treated as histidinate and hydroxide, respectively. Lys85, Arg124, Lys190, Lys231. Lys239. Lys224 and Glu302 were each neutralized by adding a counter ion ($Na^+$ or $Cl^-$), respectively. The parameters for the PME method were defined as follows: BOXX=76.5983, BOXY=71.4923, BOXZ=67.0672, ALPHA=BETA=GAMMA=90.0, NFFTX=64, NFFTY=64, NFFTZ=64, SPLINE_ORDER=4, ISCHARGED=1, EXACT_EWALD=0, DSUM_TOL=0.00001.

Simulation of Rubredoxin All the Glu, Asp and Cys residues were deprotonated while all the Lys residues were protonated. Asp21, Asp36. Asp17. Asp19. Asp35. Asp47. Glu50, Glu53, were each neutralized by adding a counter ion ($Na^+$), respectively. The parameters for the PME method were defined as follows: BOXX=46.8357, BOXY=44.5514, BOXZ=40.6069, ALPHA=BETA=GAMMA=90.0, NFFTX=49, NFFTY=49, NFFTZ=49, SPLINE_ORDER=4, ISCHARGED=0, EXACT_EWALD=0, DSUM_TOL=0.00001.

Each protein underwent a 2.0 ns MD simulation. Each of the three proteins maintained a zinc tetrahedral geometry throughout the 2.0 ns MD simulations. This is evident from the average distances between the zinc ion and its corresponding ligands (Table 4) and the average angles between the zinc ligands compared to the values measured in the X-ray structures (Table 5).

TABLE 4

Nonbonded distances (Å) calculated from the structures of the 2.0 ns MD simulations and the X-ray structures.

| | average ± deviation (no.) | |
|---|---|---|
| | MD structures | X-ray Structures |
| carboxypeptidase A* | | |
| Zn—OW (Wat$^{571}$) | 1.9 ± 0.03 (2000) | 2.0 ± 0.1 (8) |
| Zn—ND1 (H$^{69}$) | 2.1 ± 0.04 (2000) | 2.1 ± 0.07 (13) |
| Zn—ND1 (H$^{196}$) | 2.1 ± 0.04 (2000) | 2.1 ± 0.05 (13) |
| Zn—OE1 (E$^{72}$) | 2.2 ± 0.3 (2000) | 2.2 ± 0.09 (13) |
| Zn—OE2 (E$^{72}$) | 2.6 ± 0.5 (2000) | 2.3 ± 0.2 (13) |
| Zn—CD (E$^{72}$) | 2.8 ± 0.1 (2000) | 2.6 ± 0.09 (12) |
| Zn—OH (Y$^{248}$) | 17.7 ± 0.7 (2000) | 19.1 ± 0.8 (3) |
| Zn—OE1 (E$^{270}$) | 5.4 ± 0.9 (2000) | 4.7 ± 0.1 (3) |
| Zn—OE2 (E$^{270}$) | 5.2 ± 1.0 (2000) | 4.1 ± 0.06 (3) |
| Zn—CD (E$^{270}$) | 5.6 ± 0.6 (2000) | 4.9 ± 0.06 (3) |
| OW—OE1 (Wat$^{571}$, E$^{270}$) | 4.1 ± 0.8 (2000) | 3.3 ± 0.1 (3) |
| OW—OE2 (Wat$^{571}$, E$^{270}$) | 4.0 ± 1.0 (2000) | 2.6 ± 0.1 (3) |
| OW—OH (Wat$^{571}$, Y$^{248}$) | 16.1 ± 0.7 (2000) | 17.6 ± 0.8 (3) |
| carbonic anhydrase II** | | |
| Zn—OW (Wat$^{263}$) | 1.9 ± 0.02 (2000) | 2.1 ± 0.1 (17) |
| Zn—NE2 (H$^{94}$) | 2.0 ± 0.03 (2000) | 2.1 ± 0.1 (34) |
| Zn—NE2 (H$^{96}$) | 2.0 ± 0.03 (2000) | 2.1 ± 0.08 (34) |
| Zn—ND1 (H$^{119}$) | 2.0 ± 0.04 (2000) | 2.0 ± 0.1 (34) |
| Zn—NE2 (H$^{64}$) | 8.1 ± 0.7 (2000) | 8.6 ± 1.2 (31) |
| Zn—CD (E$^{106}$) | 4.5 ± 0.6 (2000) | 4.9 ± 0.06 (34) |
| Zn—OE1 (E$^{106}$) | 4.9 ± 1.0 (2000) | 5.5 ± 0.09 (34) |
| Zn—OE2 (E$^{106}$) | 3.9 ± 0.6 (2000) | 4.0 ± 0.09 (34) |
| Zn—CD (E$^{117}$) | 6.7 ± 0.2 (2000) | 7.0 ± 0.1 (31) |
| Zn—OE1 (E$^{117}$) | 7.0 ± 0.4 (2000) | 7.8 ± 0.1 (31) |
| Zn—OE2 (E$^{117}$) | 6.5 ± 0.2 (2000) | 6.6 ± 0.07 (31) |

TABLE 4-continued

Nonbonded distances (Å) calculated from the structures of the 2.0 ns MD simulations and the X-ray structures.

| | average ± deviation (no.) | |
|---|---|---|
| | MD structures | X-ray Structures |
| Zn—OG1 (T$^{199}$) | 4.4 ± 0.4 (2000) | 3.8 ± 0.1 (34) |
| Zn—OG1 (T$^{200}$) | 7.2 ± 0.5 (2000) | 6.2 ± 0.2 (33) |
| rubredoxin*** | | |
| Zn—SG (C$^{6}$) | 2.1 ± 0.04 (2000) | 2.4 ± 0.5 (1irn) |
| Zn—SG (C$^{9}$) | 2.1 ± 0.04 (2000) | 2.3 ± 0.5 (1irn) |
| Zn—SG (C$^{39}$) | 2.1 ± 0.04 (2000) | 2.4 ± 0.5 (1irn) |
| Zn—SG (C$^{42}$) | 2.1 ± 0.04 (2000) | 2.3 ± 0.5 (1irn) |

*The X-ray structures of carboxypeptidase A with resolutions higher than or equal to 2.0 Å include 5cpa, 6cpa, 1aye, 7cpa, 1bav, 8cpa, 1cbx, 3cpa, 1cpx, 1pca, 1yme, 2ctb, and 2ctc.
**The X-ray structures of carbonic anhydrase II with resolutions higher than or equal to 2.0 Å include 1ave, 1bcd, 1bic, 1bv3, 1cao, 1cil, 1cng, 1cni, 1cnj, 1cra, 1hea, 1heb, 1hec, 1hed, 1mua, 1ray, 1raz, 1uga, 1ugb, 1ugc, 1ugd, 1uge, 1ugf, 2cbd, 1ydb, 1ydc. 3ca2, 2ca2, 1ca2, 1zsb. 1zsc, 2cba, 2cbb, and 2cbc.
***The deviation of the nonbonded distance in the structure of 1irn was estimated from $\sqrt{(B_i+B_j)/(8\pi^2)}$, where $B_i$ and $B_j$ are the B values of atoms i and j, respectively.

TABLE 5

Angles (deg. of arc) calculated from the structures of the 2.0 ns MD simulations and the X-ray structures.

| | average ± deviation (no.) | |
|---|---|---|
| | MD structures | X-ray structures |
| carboxypeptidase A* | | |
| OW$^{571}$—Zn—OE1$^{72}$ | 120 ± 8 (2000) | 118 ± 8 (6) |
| OW$^{571}$—Zn—ND1$^{69}$ | 108 ± 4 (2000) | 114 ± 9 (6) |
| OW$^{571}$—Zn—ND1$^{196}$ | 107 ± 4 (2000) | 104 ± 10 (6) |
| OE1$^{72}$-Zn—ND1$^{69}$ | 123 ± 5 (2000) | 120 ± 7 (14) |
| OE1$^{72}$-Zn—ND1$^{196}$ | 88 ± 3 (2000) | 95 ± 7 (14) |
| ND1$^{69}$-Zn—ND1$^{196}$ | 102 ± 4 (2000) | 100 ± 4 (14) |
| OW$^{571}$—Zn—OE2$^{72}$ | 101 ± 8 (2000) | 92 ± 5 (6) |
| OE2$^{72}$-Zn—ND1$^{69}$ | 99 ± 11 (2000) | 99 ± 11 (14) |
| OE2$^{72}$-Zn—ND1$^{196}$ | 136 ± 16 (2000) | 149 ± 8 (14) |
| carbonic anhydrase II** | | |
| OW$^{263}$—Zn—NE2$^{94}$ | 111 ± 4 (2000) | 105 ± 5 (16) |
| OW$^{263}$—Zn—NE2$^{96}$ | 108 ± 4 (2000) | 113 ± 4 (16) |
| OW$^{263}$—Zn—ND1$^{119}$ | 107 ± 4 (2000) | 114 ± 4 (16) |
| NE2$^{94}$-Zn—NE2$^{96}$ | 109 ± 4 (2000) | 107 ± 3 (34) |
| NE2$^{94}$-Zn—ND1$^{119}$ | 115 ± 4 (2000) | 114 ± 3 (34) |
| NE2$^{96}$-Zn—ND1$^{119}$ | 106 ± 4 (2000) | 102 ± 3 (34) |
| rubredoxin*** | | |
| SG$^{6}$—Zn—SG$^{9}$ | 106 ± 4 (2000) | 113 ± 12 (1irn) |
| SG$^{6}$—Zn—SG$^{39}$ | 114 ± 4 (2000) | 112 ± 12 (1irn) |
| SG$^{6}$—Zn—SG$^{42}$ | 110 ± 4 (2000) | 105 ± 12 (1irn) |
| SG$^{9}$—Zn—SG$^{39}$ | 109 ± 4 (2000) | 104 ± 12 (1irn) |
| SG$^{9}$—Zn—SG$^{42}$ | 110 ± 4 (2000) | 112 ± 12 (1irn) |
| SG$^{39}$-Zn—SG$^{42}$ | 107 ± 4 (2000) | 112 ± 12 (1irn) |

*The X-ray structures of carboxypeptidase A with resolutions higher than or equal to 2.0 Å include 5cpa, 6cpa, 1aye, 7cpa, 1bav, 8cpa, 1cbx, 3cpa, 1cpx, 1pca, 1yme, 2ctb, and 2ctc.
**The X-ray structures of carbonic anhydrase II with resolutions higher than or equal to 2.0 Å include 1ave, 1bcd, 1bic, 1bv3, 1cao, 1cil, 1cng, 1cni, 1cnj, 1cra, 1hea, 1heb, 1hec, 1hed, 1mua, 1ray, 1raz, 1uga, 1ugb, 1ugc, 1ugd, 1uge, 1ugf, 2cbd, 1ydb, 1ydc. 3ca2, 2ca2, 1ca2, 1zsb, 1zsc, 2cba, 2cbb, and 2cbc.
***The angle deviation was estimated from ATAN(Δ D/D), where Δ D is the deviation of the SG-Zn distance (0.5 Å) and D is the SG-Zn distance (2.4 Å).

The tetrahedral geometry for a conventional zinc ion was converted to a trigonal bipyramid during the 1.0 ns simulations of carbonic anhydrase using various force field parameters of zinc developed within the paradigm of the non-bonded model. The four protein structures bound with the tetrahedral zinc molecule did not diverge from the X-ray structures during all the 2.0 ns MD simulations, which is evident from the root mean square deviations of the non-hydrogen atoms in the X-ray structure, the average structure over a 2.0 ns MD simulation (Table 6), and the interatomic distances in comparison with the values obtained from the X-ray structures.

TABLE 6

Root mean square deviation (RMSD) between the X-ray structure and the structures (excluding H, Na$^+$ and Cl$^-$ atoms) averaged over a 2.0 ns MD simulation.

| | RMSD, Å (No. of matched atoms) | | | |
|---|---|---|---|---|
| | overlay the entire protein | | overlay the zinc complex | |
| Protein | zinc | entire | zinc | entire |
| 1ca2 | 0.74 (36) | 1.28 (2045) | 0.34 | 2.89 |
| 5cpa | 0.34 (35) | 1.09 (2442) | 0.20 | 1.33 |
| 1irn | 0.52 (29) | 1.21 (417) | 0.42 | 1.34 |
| 1 dpm | 0.48 (63) | 1.11 (2525) | | |

Furthermore, the structures, interatomic distances and angles averaged over a 2.0 ns MD simulation were almost identical to the ones averaged on a 1.0 ns MD simulation.

Figure 2:
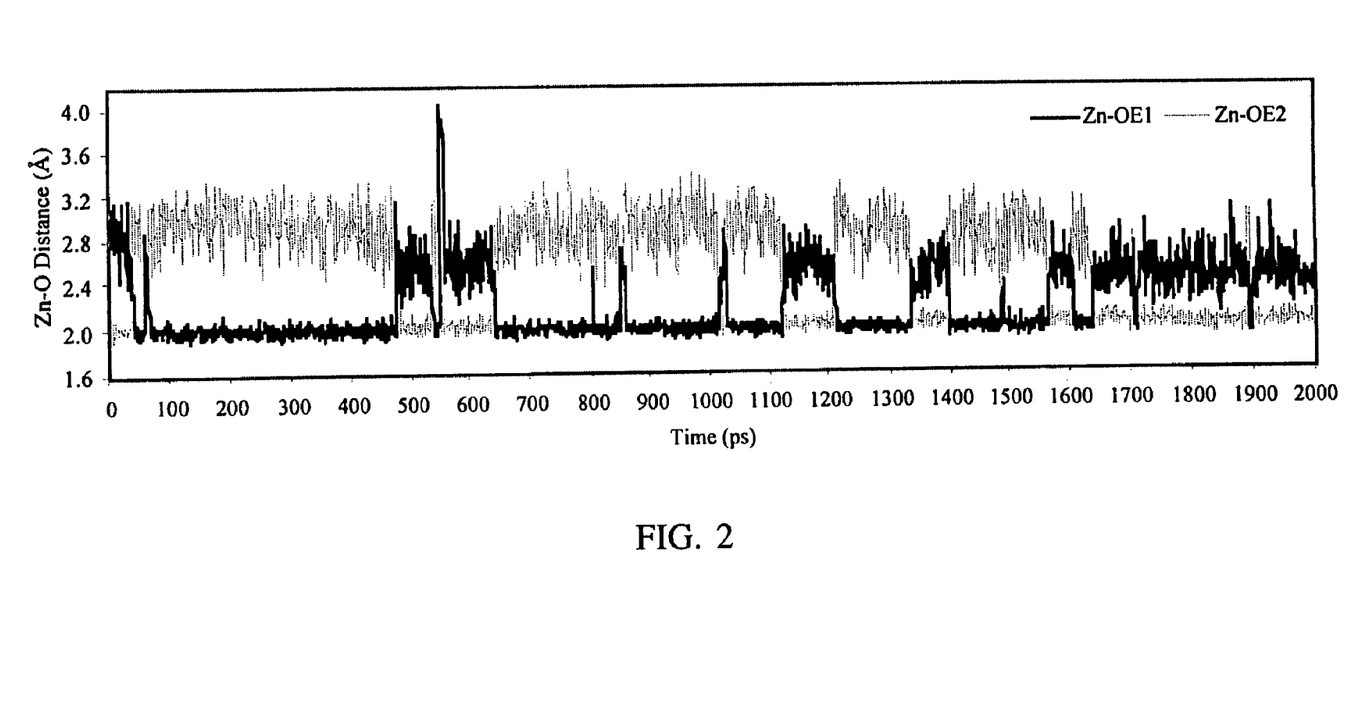
FIG. 2 depicts the simulation of the exchanges of the two oxygen atoms of the carboxylate of Glu72 as zinc's ambidentate ligand in carboxypeptidase A wherein the zinc-oxygen distances were calculated from the trajectories saved at every 1.0 picosecond (ps) interval by employing the CARNAL module of the AMBER 5.0 (TM) program.

Finally, use of the tetrahedral zinc molecule confers a simulation of the exchanges of zinc's ambidentate ligands. As depicted in FIG. 2, where the Zn-O distances close to 2.0 Å reflect that the oxygen atom coordinates to the zinc ion, the two oxygen atoms (OE1 (black colored) and OE2 (gray colored)) of the carboxylate of Glu72 alternately coordinate to Zn$^{2+}$ in the 2.0 ns simulation of carboxypeptidase A bound with the tetrahedral zinc molecule. It is worth noting that Glu72 is a bidentate ligand in the structure averaged over the 2.0 ns MD simulation (Table 2), but it is an ambidentate ligand in all the instantaneous structures in the 2.0 ns MD simulation (FIG. 2). In contrast, due to the lack of orientational preference of the zinc ligand in the reported non-bonded models, the carboxylate group of Glu72 of carboxypeptidase A can only be simulated as a pair of bidentate ligands.

EXAMPLE 2

Molecular Modeling Using Two Tetrahedral Zinc Molecules

The method of Example 1 was used to run a 2.0 nanosecond MD simulation for phosphotriesterase (PTE). This example successfully simulated the four-ligand coordination complex of two zinc ions in PTE during the MD simulation according to the crystallographic analysis of the time-average structure of the MD simulation. For comparison, phosphotriesterase was also evaluated using a conventional non-bonded model that maintains the four-ligand coordination complex with electrostatic and van der Waals forces to avoid the use of the covalent bonds that are restrained with a harmonic potential as described in Vedani and Huhta, JACS 112, 41759-67 (1990). Stote and Karplus, *Proteins* 23, 12-31 (1995), and Wasserman and Hodge, *Proteins* 24, 227-37 (1996).

Figure 3:
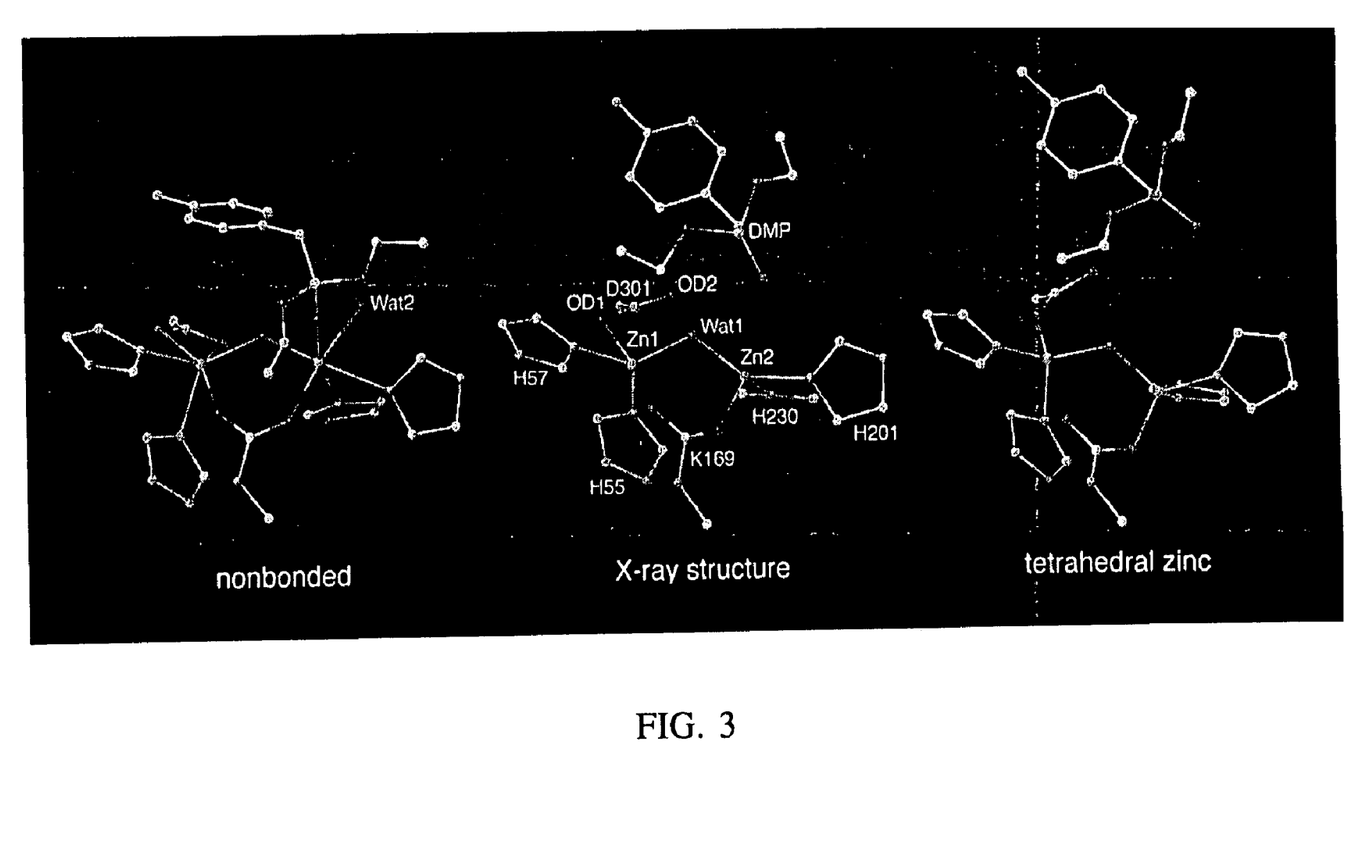
FIG. 3 depicts the stick model structure of the zinc region of phosphotriesterase determined by conventional nonbonded simulation methods, X-ray crystal derived structure, and tetrahedral zinc coordination complex simulation.

A 600 ps (2.0 fs time step) MD simulation of the zinc-bound phosphoriesterase ligand with diethyl 4-methylbenzyl phosphonate (DMP-PTE) complex was first performed using a non-bonded model with the CHARMM force field parameters for Zn$^{2+}$ ($\epsilon$=0.25 kcal/mol, r*=1.09 Å, and the formal charge of zinc ion is "+2") as described in R. H. Stote. M. Karplus, *Proteins* 23, 12-31 (1995). These parameters were reportedly adaptable to the simulation of the DMP-PTE complex with the AMBER 95 force field. See C. G. Zahn et al., *J. Am. Chem. Soc.*, 121 7279-7282 (1999). The 600 ps simulation was carried out in accordance with the reported 550 ps MD simulation of the DMP-PTE complex. The root mean square deviations (RMSDs) for the diethyl 4-methyl benzlphosphoranse (DMP), zinc bound phosphotriesterase (PTE), and their coordination complex between the X-ray structure and the time-average structure of the 600 ps MD simulation were 2.49 Å, 1.00 Å, and 1.02 Å, respectively, indicating a significant displacement in the position of DMP as compared to the X-ray structure. Although all the reported distances (Zn1-O$^{Wat1}$=2.0 Å, Zn2-O$^{Wat1}$=2.0 Å, and Zn1-Zn2=3.6 Å, (FIG. 3) calculated from the 550 ps MD simulation using non-bonded model A were identical to the distances in the time-average structure of the 600 ps MD simulation, a substantial difference of the active site between the X-ray structure and the time-average structure from the 600 ps MD simulation was observed. In the X-ray structure, one zinc ion (Zn1) was coordinating to only one carboxyl oxygen atom (Zn1-OD1=2.4 Å and Zn1-OD2=3.2 Å) of D301 (FIG. 3). In the time-average and all the instantaneous structures of the 600 ps MD simulation (FIGS. 1-2), Zn1 was coordinating to two carboxyl oxygen atoms (Zn1-OD1=2.1 Å and Zn1-OD2=2.2 Å) of D301. Similarly, two carboxyl oxygen atoms of the carbamylated lysine 169 in the X-ray structure were not coordinating to Zn1, but one of them became a coordinate of Zn1 during the 600 ps MD simulation thereby converting the four-ligand coordination of Zn1 identified in the X-ray structure to a six-ligand coordination (FIG. 3). In addition, one oxygen atom of DMP, that was 3.46 Å away from another zinc ion (Zn2) in the X-ray structure, was coordinating with Zn2 at a separation of 2.1 Å in the time-average structure of the 600 ps MD simulation (FIG. 3).

Figure 4:
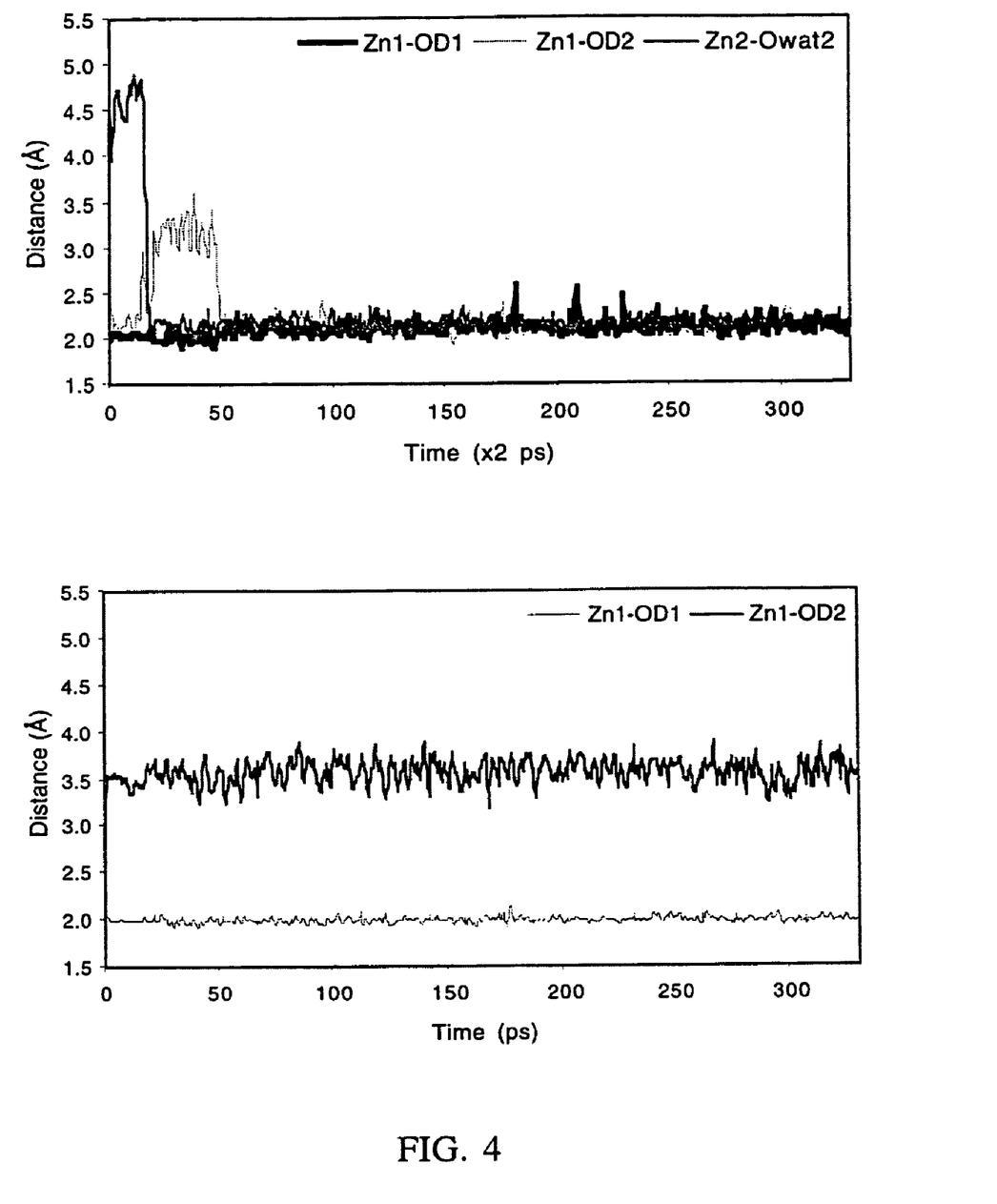
FIG. 4 depicts the distances of Zn2+ to the carbonyl O atoms of D301 and to the O atom of Wat2 that were calculated from 330 instantaneous structures using a nonbonded model suring 60 ps heating and 600 ps simulation (top) and the model described herein during 30 ps heating and 300 ps simulation (bottom), respectively.

Furthermore, one water molecule (Wat2), that was initially 5.2 Å away from Zn2, crept toward Zn2 and was kept at a distance of 2.0 Å from Zn2 during the entire 600 ps MD simulation (FIG. 4). The four-ligand coordination of Zn2 identified in the X-ray structure was thus converted to a six-ligand coordination in the non-bonded model A-based MD simulation (FIG. 3). This difference in the active site between the X-ray and MD structures, was confirmed by an extended MD simulation using non-bonded model for up to 2.0 ns and by another 1.0 ns non-bonded model-based MD simulation using a time step of 1.0 fs and a non-bonded pair list updated every 20 steps.

A 2.0 ns (1.0 fs time step) MD simulation of the DMP-PTE complex was then carried out using the methods described herein. (See also Pang, *J. Mol. Molecl.* 5:196-202 (1989)). The distance between the two heavy zinc ions in the time-average structure of the present method-based 2.0 ns MD simulation and the X-ray structure was 3.39±0.07 (2000) Å and 3.31±0.001 (2) Å, respectively, in contrast to the corresponding distance of 3.64±0.06 (1000) Å in the 2.0 ns MD simulation using non-bonded model. This result shows the accuracy of the present method in terms of the force field parameters for the zinc-zinc interactions. The four-ligand coordination complex for the two zinc ions identified in the X-ray structure were well maintained throughout the 2.0 ns MD simulation (FIG. 3 and FIG. 4).

Simulation of Phosphotriesterase using the tetrahedral zinc coordination complex. The initial structure of the DMP-PTE complex, including 67 water molecules buried inside the protein, used in the MD simulation was taken from the second subunit (segment B) of the corresponding X-ray structure (PDB code: 1 DPM). H254 was protonated; H55, H57, H201, and H230 were treated as histidinate; H123 and H257 were neutral and carried a proton attached to the epsilon nitrogen atom; E56, D100, D105, D253 were protonated; R36, R88, R89, R91, R164, R225, R356, K339, D208, D235, D236, E263, E71, and H201 were each neutralized by $Cl^-$ or $NA^+$. The water molecule (Wat1) coordinating with the two zinc divalent ions was deprotonated. The RESP charges of DMP and the carbamylated lysine were generated according to the published protocol. The RESP charges and the force field parameters of the two residues are provided in Table 6a-c.

TABLE 6a

Figure 6:
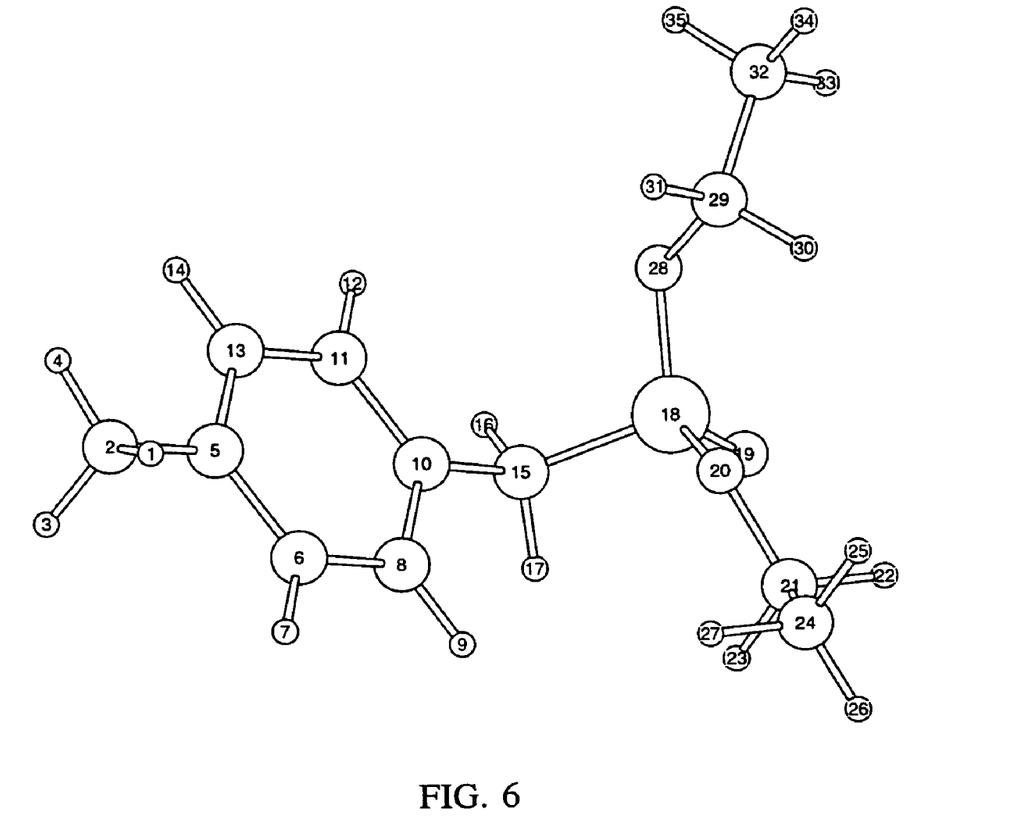
FIG. 6 depicts the 3D structure of DMP showing atom ids.

Atom Types and the RESP Charges of DMP (for atom ids, see FIG. 6).

| atom id | atom type | RESP charge (e) |
|---|---|---|
| 1 | HC | 0.061 |
| 2 | CT | −0.1824 |
| 3 | HC | 0.061 |
| 4 | HC | 0.061 |
| 5 | CA | 0.1111 |
| 6 | CA | −0.1749 |
| 7 | HA | 0.1397 |
| 8 | CA | −0.1965 |
| 9 | HA | 0.1535 |
| 10 | CA | 0.0058 |
| 11 | CA | −0.1965 |
| 12 | HA | 0.1535 |
| 13 | CA | −0.1749 |
| 14 | HA | 0.1397 |
| 15 | CT | −0.1577 |
| 16 | HC | 0.0998 |
| 17 | HC | 0.0998 |
| 18 | P | 0.8601 |
| 19 | O | −0.6401 |
| 20 | OS | −0.3566 |
| 21 | CT | 0.0805 |
| 22 | H1 | 0.0605 |
| 23 | H1 | 0.0605 |
| 24 | CT | −0.0431 |
| 25 | HC | 0.0289 |
| 26 | HC | 0.0289 |
| 27 | HC | 0.0289 |
| 28 | OS | −0.3566 |
| 29 | CT | 0.0805 |
| 30 | H1 | 0.0605 |
| 31 | H1 | 0.0605 |
| 32 | CT | −0.0431 |
| 33 | HC | 0.0289 |
| 34 | HC | 0.0289 |
| 35 | HC | 0.0289 |

TABLE 6b

Figure 7:
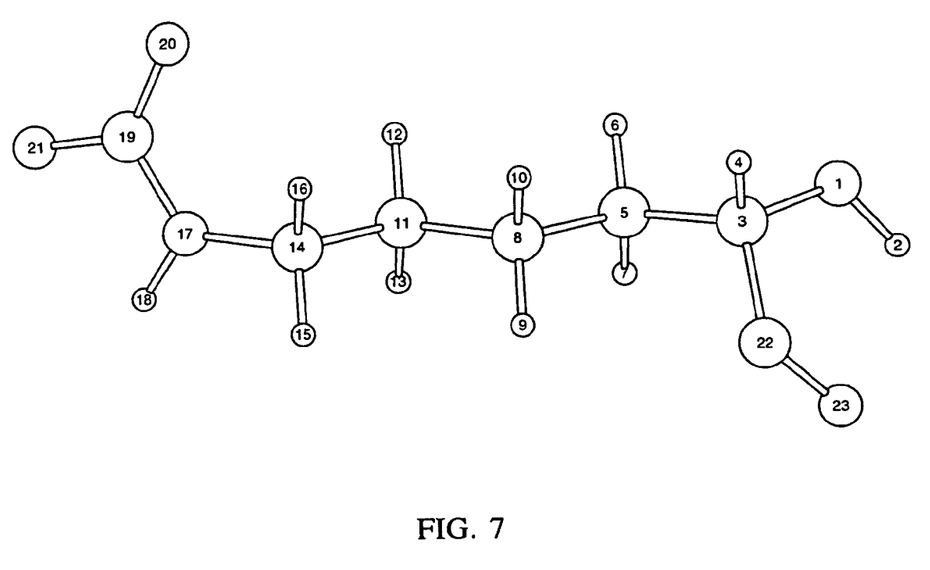
FIG. 7 depicts the 3D structure of the carbamylated lysine showing atom ids.

Atom Types and the RESP Charges of the Carbamylated Lysine (for atom ids, see FIG. 7).

| atom id | atom type | RESP charge (e) |
|---|---|---|
| 1 | N | −0.3808 |
| 2 | H | 0.2722 |
| 3 | CT | −0.0637 |
| 4 | H1 | 0.0487 |
| 5 | CT | 0.0153 |
| 6 | HC | 0.02 |
| 7 | HC | 0.02 |
| 8 | CT | −0.1343 |
| 9 | HC | 0.0378 |
| 10 | HC | 0.0378 |
| 11 | CT | −0.0766 |

TABLE 6b-continued

Atom Types and the RESP Charges of the Carbamylated Lysine (for atom ids, see FIG. 7).

| atom id | atom type | RESP charge (e) |
|---|---|---|
| 12 | HC | 0.0254 |
| 13 | HC | 0.0254 |
| 14 | CT | 0.3692 |
| 15 | HP | −0.0379 |
| 16 | HP | −0.0379 |
| 17 | N2 | −0.8693 |
| 18 | H | 0.3223 |
| 19 | C | 0.9999 |
| 20 | O2 | −0.8297 |
| 21 | O2 | −0.8297 |
| 22 | C | 0.6053 |
| 23 | O | −0.5392 |

TABLE 6c

Force Field Parameters of DMP and the Carbamylated Lysine.

| Bond | K [kcal/mol Å$^2$)] | R$_{eq}$ (Å) |
|---|---|---|
| CT-P | 230 | 1.61 |
| P—O | 525 | 1.48 |
| N2-C | 481 | 1.34 |

| angle | K [kcal/mol radian$^2$)] | T$_{eq}$ (deg.) |
|---|---|---|
| CA-CT-P | 100 | 120.5 |
| HC-CT-P | 100 | 120.5 |
| CT-P -OS | 100 | 108.23 |
| CT-N2-C | 50 | 123.2 |
| N2-C—O2 | 70 | 120 |
| H—N2-C | 35 | 120 |
| CT-P -O | 100 | 108.23 |
| O -P -OS | 100 | 108.23 |

| dihedral | IDIVF | V$_n$/2 (kcal/mol) | γ (deg.) | N |
|---|---|---|---|---|
| X -CT-P -X | 3 | 0.75 | 0 | 3 |
| X -N2-C -X | 4 | 9.6 | 180 | 2 |

| Improper dihedral | V$_n$/2 (kcal/mol) | γ (deg.) | N |
|---|---|---|---|
| X -X -CA-CA | 1.1 | 180 | 2 |

Consistent with the known X-ray structure, Zn1 in the time-average and all the instantaneous MD structures was coordinating to only one carboxyl oxygen atom (Zn1-OD1=2.0 Å and Zn1-OD2=3.6 Å) of D301 (FIGS. 1-2). Only one water molecule (Wat1) was coordinating to Zn1 and Zn2 during the entire 2.0 ns MD simulation-using model B. The RMSDs of DMP, PTE, and their complex between the X-ray structure and the time-average structure of the 2.0 ns MD simulation were 0.89 Å, 1.11 Å, and 1.11 Å, respectively, indicating the time-average structure of the simulation using the present method was essentially identical to the X-ray structure with resolution of 2.1 Å.

Figure 5:
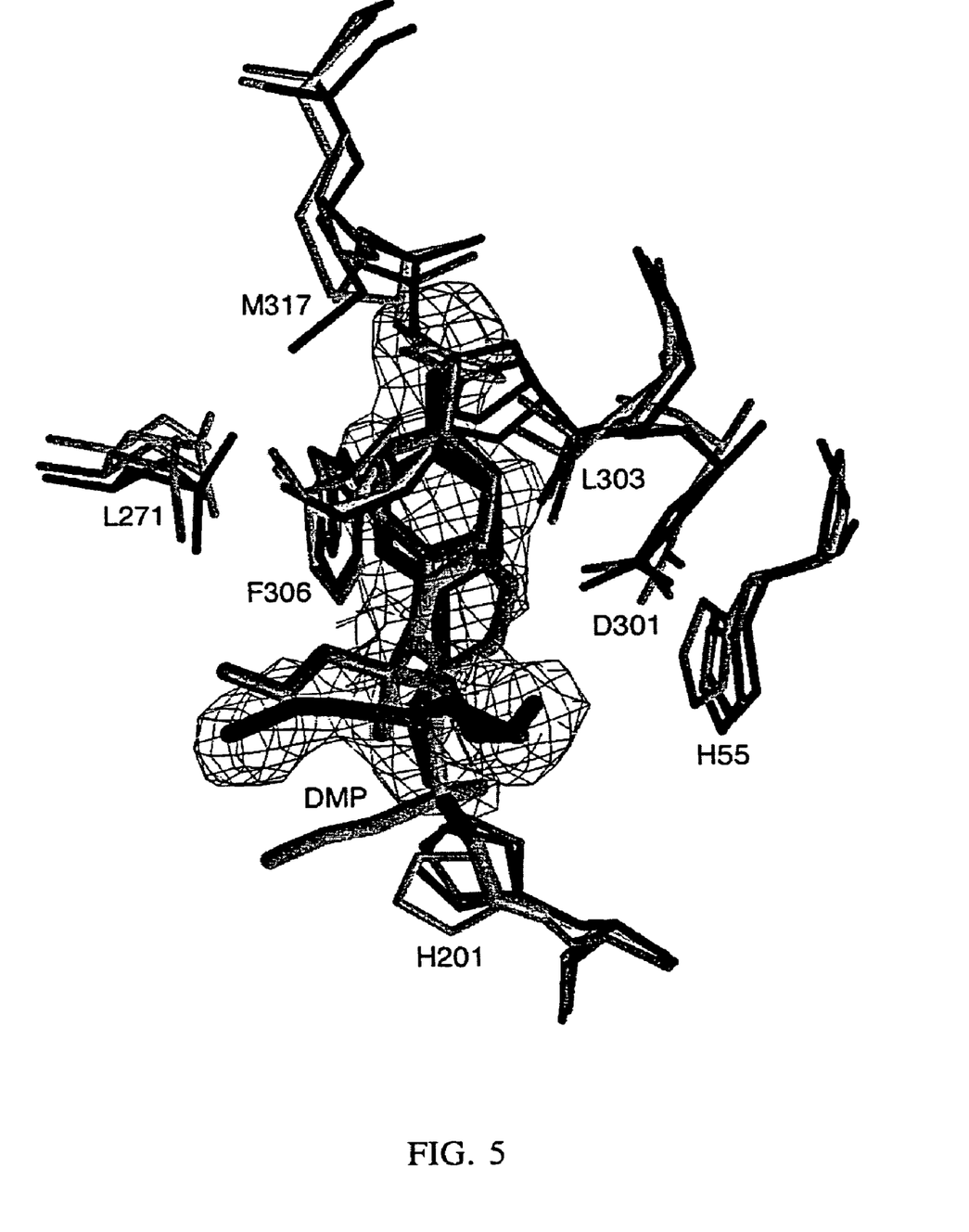
FIG. 5 depicts the $F_o$-$F_c$ map at 3.0 around DMP (thick stick model) in the X-ray structure of PTE (black) and the time-average structures of PTE derived from the 2.0 ns MD simulations using the conventional non-bonded method (cyan) and the method described herein (magenta), respectively.

Also, the time-average structure of the PTE complex derived from the MD simulation using the tetrahedral zinc ion fit into the difference electron density map of the PTE X-ray structure with DMP omitted whereas the corresponding structure obtained from the MD simulation using the conventional nonbonded method was not able to fit into the election density map (FIG. 5). The root mean square deviation between the x-ray crystal structure and the PTE structure averaged over a 2.0 ns MD simulation were 0.48 Å with 63 matching atoms for the zinc region and 1.11 Å for the entire protein with 2525 atoms matching.

The successful simulation of PTE complex using tetrahedral zinc coordination complex therefore validated not only the force field parameters for the zinc divalent action, but also the notion of using cationic dummy atoms to mimic vacant orbitals of metal ions that accommodate the lone-pair electrons of the metallic ligands thus imposing the requisite orientational requirement for the ligands and the coordination complex of metalloproteins.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A computer running a computer program, the computer program executing instructions for performing a method comprising:
    receiving information relating to a monoatomic metal ion to be simulated;
    and generating, for observation by a user on a display, a representation of the monoatomic metal ion as a metal molecule by a molecular dynamics simulation, wherein said metal molecule consists of a plurality of metal atoms comprising a center atom and one or more dummy atoms, wherein said center atom has a van der Waals radius greater than zero and has a charge of zero, wherein said center atom is covalently linked to said one or more dummy atoms, wherein each dummy atom has a positive charge, and wherein said dummy atoms are located at the apices of a polyhedron.

2. The computer of claim 1 wherein said dummy atom has a mass of about 0.1 g/mol.

3. The computer running a computer program of claim 1 wherein said dummy atom has a mass greater than about 0.1 g/mol.

4. The computer of claim 1 wherein said center atom is located at the center of said polyhedron.

5. The computer of claim 1 wherein said polyhedron is selected from the group consisting of tetrahedron, trigonal bipyramid, square pyramid, and octahedron.

6. The computer of claim 1 wherein said polyhedron is a tetrahedron.

7. The computer of claim 1 wherein said metal ion is selected from a main group metal or transition metal.

8. The computer of claim 1 wherein said metal ion is selected from the group consisting of zinc, cadmium, mercury, copper, nickel, cobalt, iron, manganese, calcium, and magnesium.

9. The computer of claim 1 wherein said metal ion is zinc.

10. The computer of claim 1 wherein said metal ion is nickel.

11. The computer of claim 1 wherein said metal ion is magnesium.

12. The computer of claim 1 wherein said metal ion is calcium.

13. The computer of claim 1 wherein said metal ion has a calculated energy of solvation about equal to an experimentally determined energy of solvation for said metal ion.

14. The computer of claim 13 wherein said calculated energy of solvation is within about 10% of said experimentally determined energy of solvation for said metal ion.

15. The computer of claim 1 wherein said dummy atom has a charge of about +0.5.

16. The computer of claim 1 wherein said dummy atom has a charge of about +0.3333.

17. The computer of claim 1 wherein said dummy atom has a charge ranging from about +0.1 to about +3.

* * * * *

UNITED STATES PATENT AND TRADEMARK OFFICE
CERTIFICATE OF CORRECTION

PATENT NO. : 7,664,625 B2 Page 1 of 1
APPLICATION NO. : 10/723594
DATED : February 16, 2010
INVENTOR(S) : Yuan-Ping Pang It is certified that error appears in the above-identified patent and that said Letters Patent is hereby corrected as shown below:

Title Page, Item (56) References Cited, Other Publications, Maggiora, please delete "pophines" and insert --porphyrins-- therefor;

Title Page, Item (56) References Cited, Other Publications, Maggiora, please delete "Chemcial" and insert --Chemical-- therefor;

Column 3, line 62, please delete "Zn2+" and insert --$Zn^{2+}$-- therefor;

Column 15, line 9, please delete "NA" and insert --Na-- therefor.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO.      : 7,664,625 B2                                   Page 1 of 1
APPLICATION NO. : 10/723594
DATED           : February 16, 2010
INVENTOR(S)     : Yuan-Ping Pang It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 301 days.

Signed and Sealed this

Thirtieth Day of November, 2010

David J. Kappos
*Director of the United States Patent and Trademark Office*